(12) United States Patent
Massimo, Sr.

(10) Patent No.: US 6,260,885 B1
(45) Date of Patent: Jul. 17, 2001

(54) LATENT FINGERPRINT LIFTING AND RECORDATION DEVICE

(76) Inventor: John M. Massimo, Sr., 2407 Falcon Ct., Bradenton, FL (US) 34209

( * ) Notice: Subject to any disclaimer, the term of this patent is extended or adjusted under 35 U.S.C. 154(b) by 0 days.

(21) Appl. No.: 09/653,067

(22) Filed: Sep. 1, 2000

(51) Int. Cl.[7] .................................................. B42D 15/00
(52) U.S. Cl. .............................. 283/68; 283/78; 283/84; 283/900; 462/8; 462/17
(58) Field of Search .............................. 283/68, 69, 900, 283/115, 78, 84, 100, 103, 104; 462/84, 817

(56) References Cited

U.S. PATENT DOCUMENTS

| | | | |
|---|---|---|---|
| 1,607,946 | * 11/1926 | Crosskey | 283/68 |
| 2,007,589 | * 7/1935 | Pierce | 283/68 |
| 2,048,879 | * 7/1936 | Moran . | |
| 3,419,287 | * 12/1968 | Rudie . | |
| 3,694,240 | * 9/1972 | Miller et al. . | |
| 3,867,164 | * 2/1975 | Orlando et al. | 283/68 |
| 3,959,884 | * 6/1976 | Jordan et al. | 283/68 |
| 4,325,570 | * 4/1982 | Estrada | 283/68 |
| 4,706,600 | 11/1987 | Mason et al. . | |
| 5,078,426 | 1/1992 | Reardon . | |
| 5,114,188 | 5/1992 | Koch . | |
| 5,281,293 | 1/1994 | Frame et al. . | |
| 5,390,680 | 2/1995 | Brenner . | |

OTHER PUBLICATIONS

Sirchie Fingerprint Laboratories Catalog, p. 91.
ODV Fingerprinting & Crime Scene Catalogue.
Lightning Powder Company, Inc. Catalog, p. 10.
Ace Fingerprint Equipment Laboratories, Inc. Catalog, p. 11.
Lynn Peavey Company 1999 Crime Scene Investigator's Product Guide, p. 21.

* cited by examiner

*Primary Examiner*—A. L. Wellington
*Assistant Examiner*—Monica S. Carter
(74) *Attorney, Agent, or Firm*—Charles J. Prescott

(57) ABSTRACT

A latent fingerprint lifting and recordation device of the type which provides a permanent and official fingerprint document. The device includes a flexible transparent latent fingerprint lifting sheet having one adhesive surface thereof and a flat opaque flexible frame having an open central area and being substantially similar in size and shape to that of, and adhered in generally coextensive fashion on one surface thereof against the fingerprint lifting sheet. A majority of the adhesive surface is exposable and unattached over said open central area for lifting a latent fingerprint. A flat protective cover is positioned against, and similar in size and shape to, that of the frame and releasably adhered against the adhesive surface through the open central area. When the transparent fingerprint lifting sheet, with the frame adhesively attached thereto, are removed from the cover, an imaged latent fingerprint may be lifted and recorded on the adhesive surface, the latent fingerprint thereafter protectively sandwiched for viewing through the transparent sheet when the cover is adhesively reattached to the adhesive surface to form a permanent fingerprint document.

4 Claims, 3 Drawing Sheets

LATENT FINGERPRINT LIFTING AND RECORDATION DEVICE

BACKGROUND OF THE INVENTION

1. Scope of Invention

This invention relates generally to the field of taking and recording fingerprints, and more particularly to a device for the lifting and recordation of latent fingerprints into a permanent document for later official use.

2. Prior Art

The lifting of latent fingerprints is traditionally done in its most economical fashion by using a length of one-sided adhesive transparent packing tape. A length of such tape is simply applied directly over the latent print once it has been identified and powder treated or imaged for enhanced viewability by then simply pressing the adhesive surface of the tape segment directly atop the fingerprint and thereafter simply removing the tape carrying with it the fingerprint image attached thereto.

The lifted latent fingerprint is then typically adhesively attached to a stiff opaque card and labeled appropriately. However, the end product, which may be depended upon for use at trial and the like, has a generally unprofessional and inconsistent appearance and, for the truly professional law enforcement agents, further mounting and preparation into a more formal document for such use is desirable.

A device for lifting and processing latent fingerprints has been invented by Frame and is shown in U.S. Pat. No. 5,281,293. This device is directed to applying fingerprint lifting tape to imaged residues via an arcuate base member with a handle means for providing a rocking motion to the arcuate base member while it carries a releasably attachable length of lifting tape applied to the outside of the arcuate member.

Mason, in U.S. Pat. No. 4,706,600 teaches another kit for making sets of transparent fingerprints utilizing a differential adhesion concept, the device including a backing adhesive sheet, a centrally positioned transparent adhesive print strip and a protective cover.

Another fingerprint recording device has been invented by Reardon as disclosed in U.S. Pat. No. 5,078,426 teaching a protected area for the recording and preservation of a latent fingerprint attached over a portion of an identifying card and providing for the removal of the fingerprint for further forensic and verification processes.

In U.S. Pat. No. 5,114,188, Koch discloses a fingerprinting system and method for taking and developing fingerprints in a formal setting wherein the subjects' fingers are cleansed of dirt and chemicals. The fingerprint is recorded on a layer of adhesive adhered to a sheet of transparent material which is then developed by making a copy of the sensitized surface by back reflecting radiant energy.

A method of taking limb impressions is disclosed by Brenner in U.S. Pat. No. 5,390,680 wherein the impression of a limb such as a foot or hand may be prepared for mail order or catalog sales for shoes and gloves and shoe inserts without the need for direct sizing.

An unpatented device shown in current catalogs such as those distributed by Sirchie Fingerprint Laboratories, ODV Fingerprinting and Crime Scene Catalogue, Lightning Powder Company, Inc., and Ace Fingerprint Equipment Laboratories, Inc., as a latent fingerprint device is generally characterized as having a transparent fingerprint lifter hingedly attached along one common margin to an underlying rigid opaque panel, the fingerprint, once taken onto the adhesive surface of either the opaque panel or the transparent sheet, being preserved after the two are resandwiched back together. Although listed in the above-referenced catalogs, this unpatented device has clearly not made its presence well known in the marketplace as applicant, who has been associated with law enforcement for nearly three decades, has never encountered this device in the field of crime investigation.

The present invention provides an economical to manufacture and easily useable latent fingerprint lifting and recordation device which not only facilitates the easy lifting of a latent fingerprint, but also provides an immediately available permanent recordation document of the latent print which is professional in appearance for use in both legal and financial verification settings.

BRIEF SUMMARY OF THE INVENTION

This invention is directed to a latent fingerprint lifting and recordation device of the type which provides a permanent and official fingerprint document. The device includes a flexible transparent latent fingerprint lifting sheet having one adhesive surface thereof and a flat opaque flexible frame having an open central area and being substantially similar in size and shape to that of, and adhered in generally coextensive fashion on one surface thereof against the fingerprint lifting sheet. A majority of the adhesive surface is exposable and unattached over said open central area for lifting a latent fingerprint. A flat protective cover is positioned against, and similar in size and shape to, that of the frame and releasably adhered against the adhesive surface through the open central area. When the transparent fingerprint lifting sheet, with the frame adhesively attached thereto, are removed from the cover, an imaged latent fingerprint may be lifted and recorded on the adhesive surface, the latent fingerprint thereafter protectively sandwiched for viewing through the transparent sheet when the cover is adhesively reattached to the adhesive surface to form a permanent fingerprint document.

It is therefore an object of this invention to provide a latent fingerprint lifting and recordation device formed as a unit which may be easily temporarily separable for lifting a latent fingerprint and then recombined into a single professional document recording the fingerprint for later professional, legal and financial use as required.

It is another object of this invention to provide a latent fingerprint lifting and recordation device having the provision for proper recordation of all associated information related to the fingerprint which is permanently viewably displayed on the device.

It is still another object of this invention to provide a latent fingerprint lifting and recordation device which will as easily useable and adoptable by law enforcement as a more simple and economical means than that currently in use for lifting latent fingerprints, but which lack any substantial aspects of permanency and professional display of critical evidence for later legal use.

Yet another object of this invention is to provide a latent fingerprint lifting and recordation device which prevents the crime scene investigator from inadvertently touching the sticky surface of the tape and prevents the tape from wrinkling and sticking to itself.

In accordance with these and other objects which will become apparent hereinafter, the instant invention will now be described with reference to the accompanying drawings.

DETAILED DESCRIPTION OF THE INVENTION

Figure 1:
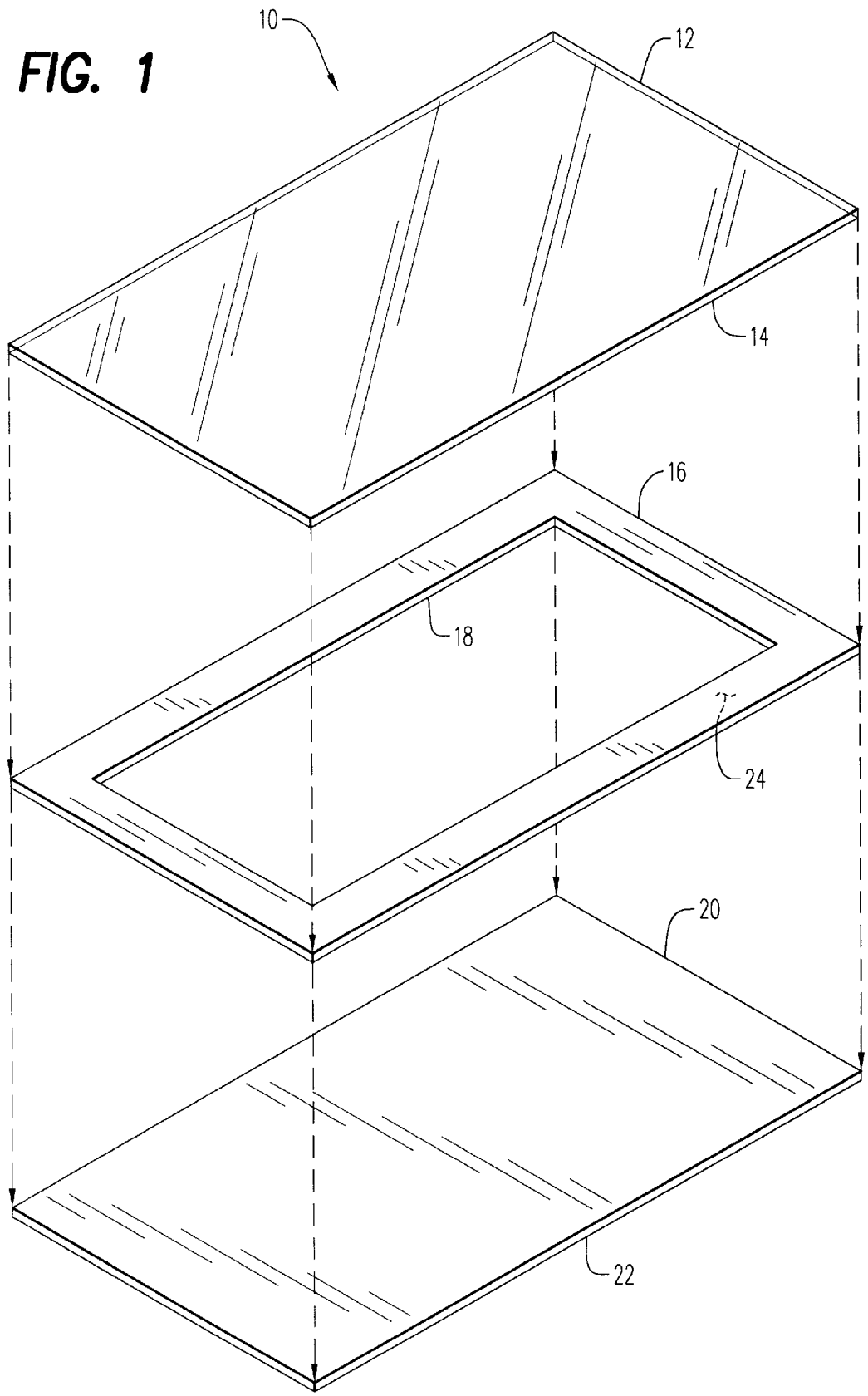
FIG. 1 is an exploded perspective view of the invention.
Figure 2:
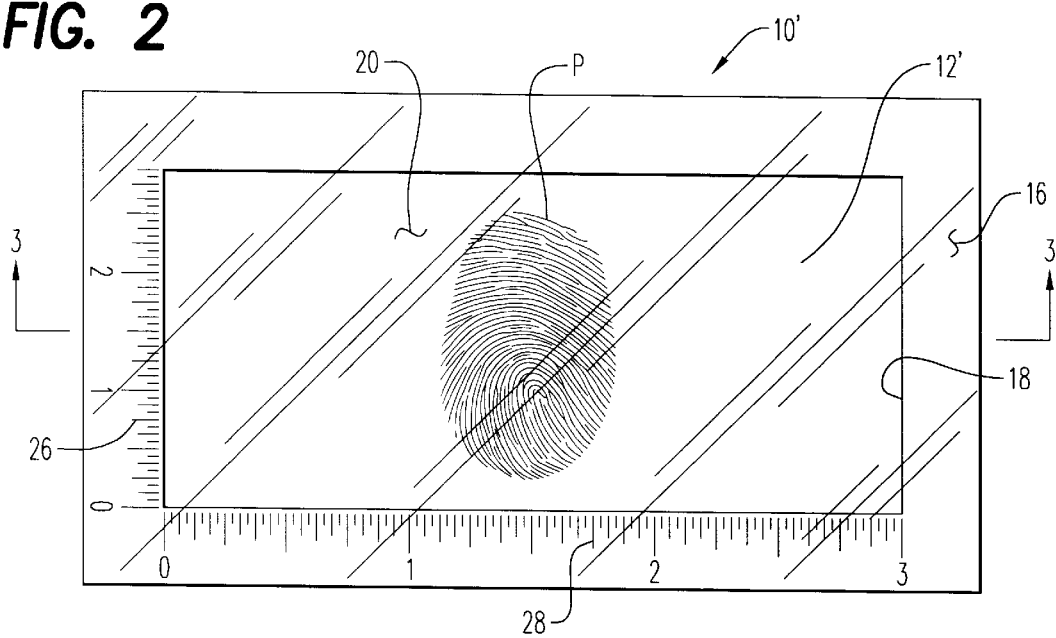
FIG. 2 is a top plan view of the invention after a latent fingerprint has been lifted and recorded.
Figure 3:
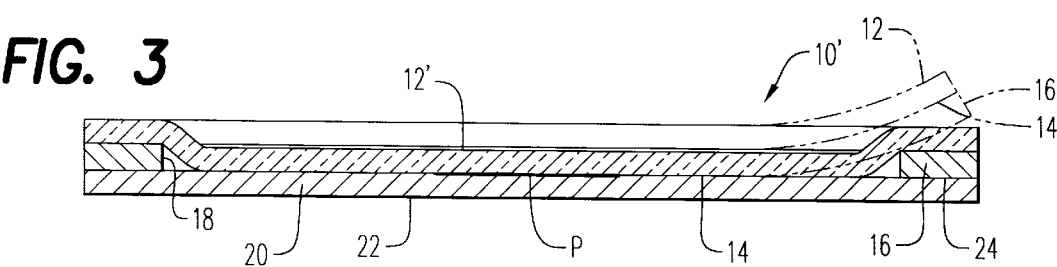
FIG. 3 is a section view in the direction of arrows 3—3 in FIG. 2.
Figure 4:
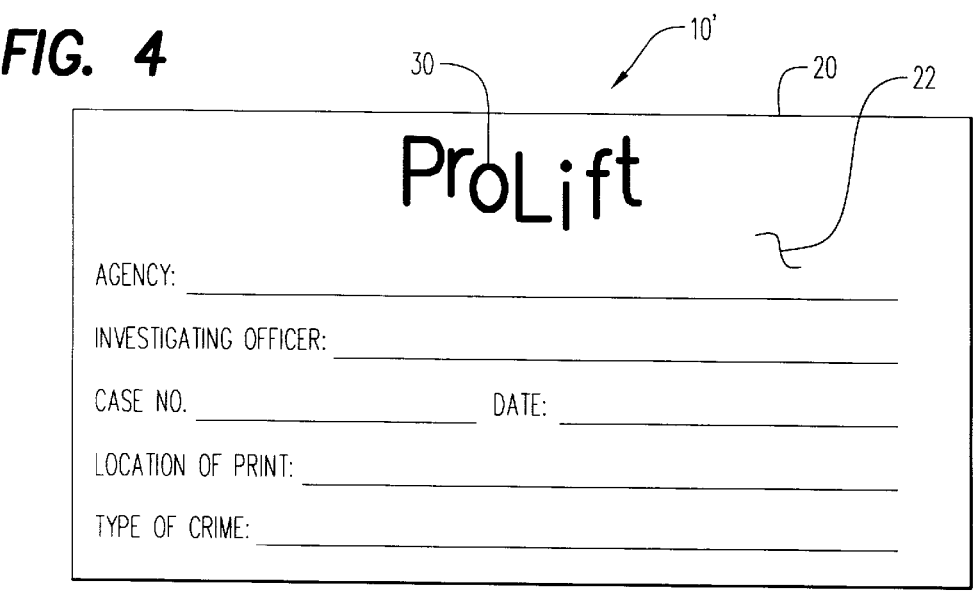
FIG. 4 is a back plan view of the reverse side of the invention of FIG. 1.

Referring now to the drawings, the invention is shown in FIG. 1 generally at numeral 10 prior to use and at 10' in FIGS. 2, 3 and 4 after being used to lift a fingerprint P and includes a rectangular flexible transparent fingerprint lifting sheet 12 having an adhesive surface 14 on one side thereof. The adhesive surface 14 is adhered substantially permanently against a flexible rectangular frame 16 formed of heavy paper or plastic having an enlarged central rectangular opening 18 formed therethrough. The margins of the transparent sheet 12 and the frame 16 are substantially similar.

The invention 10 further includes an opaque flexible cover sheet 22, again substantially similar in overall size and width to that of the adhesive sheet 12 and frame 16. There is no adhesive attachment between the mating surfaces 24 between the frame 16 and the protective cover sheet 20. A portion of the adhesive surface 14 which does come in contact directly against the frame 16 and adhesively extends across the open central portion 18, contacting against and releasably adhered to the majority of the surface of the protective cover 20.

As best seen in FIG. 2, the obverse surface of the frame 16 includes distance scales 26 and 28 extending along the respective orthogonal margins of the central opening 18 so that there is a convenient means for assessing the overall size of a latent fingerprint P as it appears in FIG. 2.

The reverse surface 22 of the protective cover 20 as seen in FIG. 4 includes provision for recording important information 30 associated with each latent fingerprint P which has been lifted and appears on the obverse surface of the device 10' as shown in FIG. 2. This information 30 is directed to such items as the recordation of the agency that took the fingerprint, the officer conducting the investigation and other pertinent information, including the location where the latent fingerprint was found and taken.

Figure 5:
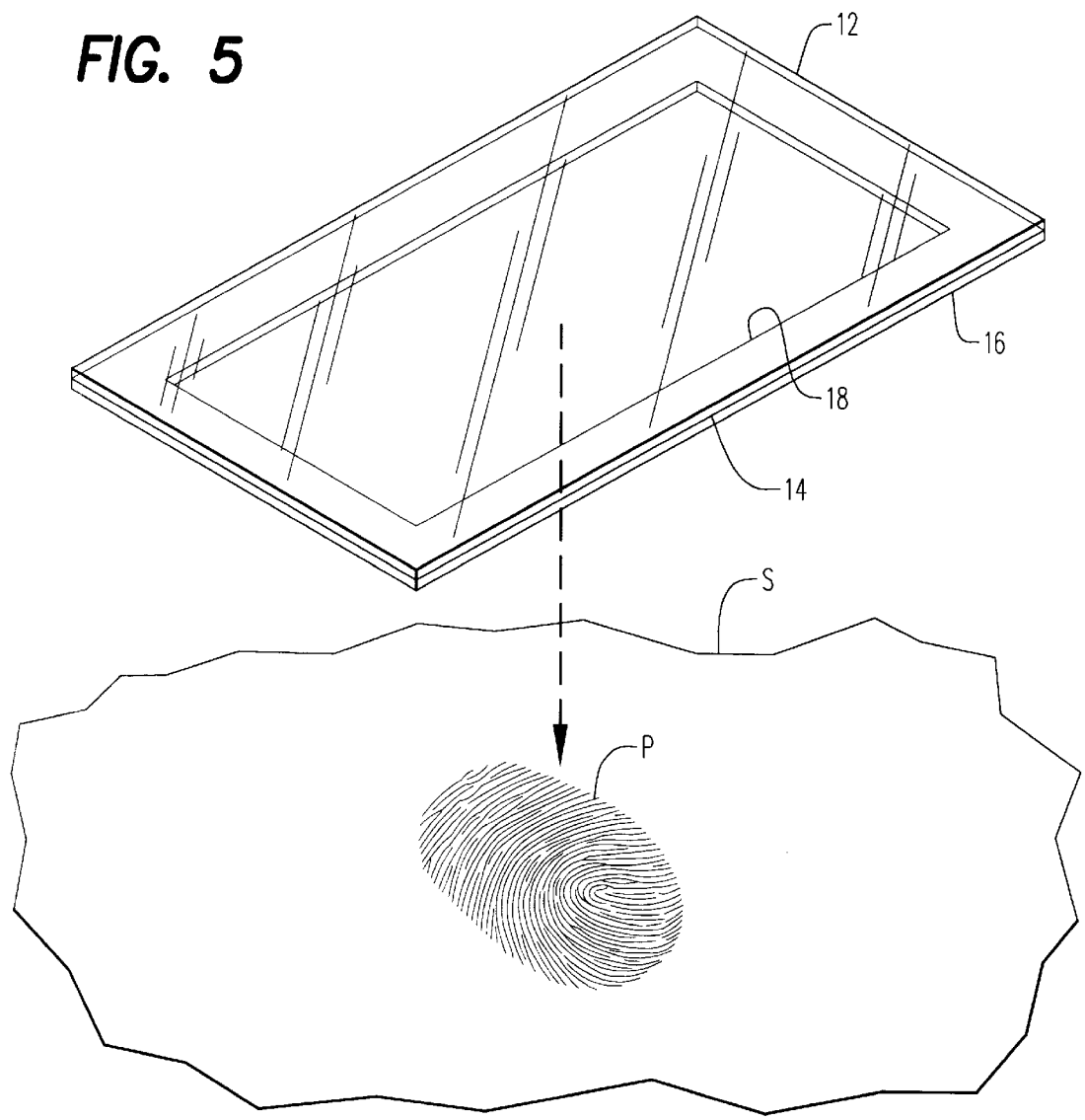
FIG. 5 is a perspective view of the invention absent the protective cover and shown in a position ready to lift a latent fingerprint on a substrate.

To use the device 10, the frame 16, formed of flexible heavy paper, cardboard or plastic sheet material, is separated from the protective cover sheet 20, along with the transparent one-sided adhesive sheet 12 shown being removed in phantom in FIG. 3. Note that the unadhered surface 24 between the frame 16 and the protective cover 20 facilitates easy separation. Once the protective cover 20 is separated from the frame and adhesive sheet 12, as best seen in FIG. 5, the two-part arrangement of frame 16 carrying the transparent adhesive sheet 12 may be applied over a viewably enhanced or imaged fingerprint P which has been enhanced by conventional methods such as the application of powder. The imaged latent fingerprint P is then attached to the adhesive surface 14 in a central location so that it may be viewable within the opening 18 of frame 16, again as best seen in FIG. 2.

A further benefit to the frame 16 and the rigidity provided thereby is the prevention of the adhesive sheet 12 from inadvertently folding or wrinkling and becoming attached to itself as is likely the case using other conventional adhesive tape means for lifting fingerprints. Moreover, the crime scene investigator is substantially less likely to inadvertently touch the sticky surface of the adhesive sheet 12 and thereby render it useless.

Although the invention 10 is as described herein as being typically applicable to a single fingerprint, the overall size, length and width, may be easily be varied within the scope of this invention so that a complete set of prints, a palm print, or other latent indicia of hand or foot identification may be lifted onto the adhesive surface of the transparent sheet supported by the flexible frame attached around the perimeter thereof.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A latent fingerprint lifting and recordation device of the type which provides a permanent and official fingerprint document, said device comprising:

a flexible transparent latent fingerprint lifting sheet having one adhesive surface thereof;

an opaque flexible frame having an open central area and substantially similar In size and shape to that of, and adhered in generally coextensive fashion on one surf thereof, to said fingerprint lifting sheet, a majority of said adhesive surface exposable and unattached over said open central area for lifting a latent fingerprint;

a protective cover positioned against, and similar in size and shape to, that of said frame and releasably adhered against said adhesive surface through said open central area;

whereby, when said fingerprint lifting sheet with said frame adhesively attached thereto are removed from said cover, an imaged latent fingerprint may be lifted and recorded on said adhesive surface, the latent fingerprint thereafter protectively sandwiched for viewing through said fingerprint lifting sheet when said cover is adhesively reattached to said adhesive surface to form a permanent fingerprint document;

said frame included scale measurement indicia printed thereon positioned adjacent said open central area for size comparison to a latent fingerprint on said fingerprint lifting sheet.

2. A latent fingerprint lifting and recordation device as set forth in claim 1, wherein:

an obverse surface of said protective cover includes printed information recordation data related to the latent fingerprint taken on said fingerprint lifting sheet.

3. A latent fingerprint lifting device of the type which provides a permanent and official fingerprint document, said device comprising:

a flexible flat transparent sheet having one adhesive surface thereof of a type capable of lifting an imaged latent fingerprint;

a flat opaque flexible frame having a central opening and adhered in generally coextensive fashion against said adhesive surface, a majority of said adhesive surface exposable and unattached to said frame over said central opening for lifting a latent fingerprint;

a protective cover positioned against, and substantially coextensive with said frame and releasably adhered against said adhesive surface through said central opening;

whereby, when said transparent sheet with said frame adhesively attached thereto are removed from said cover, a latent fingerprint may be lifted and recorded on said adhesive surface, the latent fingerprint thereafter protectively sandwiched for viewing through said transparent sheet when said cover is adhesively reattached to said adhesive surface to form a permanent fingerprint document;

said frame included scale measurement indicia printed thereon positioned adjacent said open central area for size comparison to a latent fingerprint on said fingerprint lifting sheet.

4. A latent fingerprint lifting and recordation device as set forth in claim 3, wherein:

an obverse surface of said protective cover includes printed information recordation data related to the latent fingerprint taken on said fingerprint lifting sheet.

* * * * *